US006635803B1

(12) United States Patent
Schroeder et al.

(10) Patent No.: US 6,635,803 B1
(45) Date of Patent: Oct. 21, 2003

(54) METHOD TO IMPROVE DROUGHT TOLERANCE IN PLANTS

(75) Inventors: Julian I. Schroeder, LaJolla, CA (US); June Myoung Kwak, San Diego, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/567,730

(22) Filed: May 10, 2000

Related U.S. Application Data
(60) Provisional application No. 60/170,458, filed on Dec. 13, 1999.

(51) Int. Cl.⁷ ........................ C12N 15/82; C12N 15/79; A01H 5/00
(52) U.S. Cl. ................... 800/278; 435/320.1; 435/468; 800/298
(58) Field of Search .............................. 435/320.1, 419, 435/468; 800/278, 298

(56) References Cited

FOREIGN PATENT DOCUMENTS

WO          99/31259        6/1999        ........... C12N/15/82

OTHER PUBLICATIONS

Schachtman, "Molecular insights into the structure and function of plant K+ transport mechanims", 2000, Biochimica et Biophysica Acta 1465, pp. 127–139.*

Ichida et al, Expression of a Cs+–Resistant Guard Cell K+ Channel Confers Cs+–Resistant, Light–Induced Stomatal Opening in Transgenic Arabidopsis, 1997, The Plant Cell vol. 9, pp. 1843–1857.*

Kwak, J.M., et al., "Dominant negative guard cell K+ channel mutants inhibit light–induced stomatal opening in Arabidopsis", *Abstract for 10th International Conference on Arabidopsis Researach, Melbourne, Australia, Jul. 4–8, 1999.*

Kwak, J.M., et al., "Dominant negative guard cell K++ channel mutants inhibit stomatal opening in Arabidopsis (Abstract)", *American Society of Plant Physiologists, Baltimore, MD*, (Jul. 24–28, 1999).

Baizabal–Aguirre, V.M., et al., "Suppression of Inward–Rectifying K+ Channels KAT1 and AKT2 by Dominant Negative Point Mutations in the KAT1 Alpha–Subunit", *J. Membrane Biol.*, vol. 167, 119–125, (1999).

Hetherington, A.M., "Plant physiology: spreading a drought warning", *Current Biology*, vol. 8, No. 25, XP000926453, R611–R913, (Dec. 1998).

Kopka, J., et al., "Potato guard cells respond to drying soil by a complex change in the expression of genes related to carbon metabolism and turgor regulation", *Plant Journal*, vol. 11, No. 1, XP012147520, 871–882, (1997).

Kwak, J.M., et al., "Dominant negative guard cell K+ channel mutants reduce inward–rectifying K+ currents and light–induced stomatal opening in Arabidopsis", *Plant physiology*, vol. 127, 473–485, (Oct. 2001).

Maathuis, F.J., et al., "Roles of Higher Plant K+ Channels", *Plant Physiology*, vol. 114, No. 4, XP001002310, 1141–1149, (1997).

Muller–Robert, B., et al., "Cloning and electrophysiological analysis of KST1, an inward rectifying K+ channel expressed in potato guard cells", *Embo J.*, vol. 14, No. 11, XP002099754, 2409–2418, (1995).

Schroeder, J.I., et al., "Perspectives on the physiology and structure of inward–rectifying K+ channels in higher plants: biophysical implications for K+ uptake", *Annual Rev. of Biophysics & Biomolcular Structure*, vol. 23, XP0020870447, 441–471, (1994).

Schwartz, A., et al., "Inhibition of inward K+ channels and stomatal response by abscisic acid: an intracellular locus of phytohormone action", *Proc. of the Nat'l Aca. of Sci*, vol. 91, No. 9, XP002189113, 4019–4023, (1994).

Torsethhaugen, G., et al., "Ozone inhibits guard cell K+ channels implicated in stomatal opening", *Proc. of the Nat'l Aca. of Sci. of the US*, vol. 96, No. 23, XP002189112, 13577–13582, (Nov. 9, 1999).

Maser, Pascal.,et al. ,"Phylogenetic Relationships Within Cation Transporter Families of Arabidopsis", *Plant Physiology*, vol. 126 (Aug. 2001), 1646–1667.

Uozumi, Nobuyuki.,et al. ,"Identification of Strong Modifications in Cation Selectivity in an Arabidopsis Inward Rectifying Potassium Channel by Mutant Selection in Yeast", *The Journal of Biological Chemistry*, vol. 270, No. 41(1995), 24276–24281.

* cited by examiner

*Primary Examiner*—Elizabeth F. McElwain
*Assistant Examiner*—Cynthia Collins
(74) *Attorney, Agent, or Firm*—Schwegman, Lundberg, Woessner & Kluth, P.A.

(57) ABSTRACT

A method to increase drought resistance in plants is provided. The method comprises inhibiting or disabling inward-rectifying $K^+$ ($K^+_{in}$) channels in the stomatal guard cells of the plant.

18 Claims, 7 Drawing Sheets

METHOD TO IMPROVE DROUGHT TOLERANCE IN PLANTS

CLAIM OF PRIORITY

This application claims priority under 35 U.S.C. 119(e) from U.S. Provisional Application Serial No. 60/170,458, filed Dec. 13, 1999, which application is made a part hereof by reference.

STATEMENT OF GOVERNMENT RIGHTS

The invention was made, at least in part, with a grant from the Government of the United States of America (grant FG03-94-ER20148 from the Department of Energy and grant MCB-9506191 from the National Science Foundation). The Government may have certain rights in the invention.

BACKGROUND OF THE INVENTION

Unpredictable rainfall, increases in soil salinity, and low temperature at the beginning or end of the growing season often result in decreased plant growth and crop productivity. These three environmental factors share at least one element of stress and that is water deficit or dehydration.

Drought is a significant problem in agriculture today. Over the last 40 years, for example, drought accounted for 74% of the total U.S. crop losses of corn (U.S. Department of Agriculture, 1990. Agricultural Statistics. U.S. Government Printing Office, Washington, D.C.). To sustain productivity under adverse environmental conditions, it is important to provide crops with a genetic basis for coping with water deficit, for example, by breeding water retention and/or drought tolerance mechanisms into crops so that they can grow and yield under these adverse conditions.

When the rate of transpiration exceeds that of water uptake or supply, water deficit occurs and wilting symptoms appear. The responses of plants to water deficits include leaf rolling and shedding, stomata closure, leaf temperature increases, and wilting. Metabolism is also profoundly affected. General protein synthesis is inhibited and significant increases in certain amino acid pools, such as proline, become apparent (Barnett et al., 1966). During these water deficit periods, the photosynthetic rate decreases with the ultimate result of loss in yield (Boyer, 1976). If carried to an extreme, severe water deficits result in death of the plant.

Moreover, fresh water is increasingly becoming a scarce and threatened resource in large part due to agricultural production (Serageldin, 1995). Some studies have suggested that partial reduction in stomatal apertures could optimize $CO_2$ and $H_2O$ exchange, particularly in light of rising atmospheric $CO_2$ levels (Morison et al., 1987) and thus optimize $CO_2$ flow into leaves for photosynthesis and water loss through transpiration. Classical studies showed that light-induced stomatal opening is mediated by $K^+$ and anion accumulation in guard cells (Imamura, 1943; Humble et al., 1971). Biophysical, second messenger regulation and physiological studies have suggested inward-rectifying $K^+$ ($K^+_{in}$) channels provide a major pathway for $K^+$ uptake into guard cells during stomatal opening (Schroeder et al., 1994; Müller-Röber et al., 1998).

In addition to its role in stomatal movements (Schroeder et al., 1984; Schroeder et al., 1987; Schroeder et al., 1994; MacRobbie, 1998; Müller-Röber et al., 1998), $K^+_{in}$ channels have been proposed to function in $K^+$ uptake in roots (Findlay et al., 1994; Gassmann et al., 1994; Maathuis et al., 1995; Roberts et al., 1995; Hirsch et al., 1998), leaf movements (Kim et al., 1993), and nutrient transport in vascular tissues (Wegner et al., 1994; Gaymard et al., 1998). Molecular analyses of insertional disruption mutants in the Arabidopsis $K^+$ channel genes AKT1 and SKOR1 provide further evidence for roles of $K^+$ channels in $K^+$ uptake in roots (Hirsch et al., 1998) and in $K^+$ release into the xylem sap (Gaymard et al., 1998). However, molecular physiological analyses of the functions of other plant $K^+$ channels have not yet been reported.

KAT1, a $K^+_{in}$ channel protein, is expressed predominately in guard cells (Müller-Röber et al., 1995; Nakamura et al., 1995). Transgenic Arabidopsis that express a mutant of the Arabidopsis KAT1, which has a reduced sensitivity to $Cs^+$ block, were demonstrated to exhibit partial light-induced stomatal opening in the presence of $Cs^+$ concentrations that ordinarily inhibit stomatal opening in wild-type (Ichida et al., 1997). While Ichida et al. (1997) provide molecular evidence that transgenic $K^+_{in}$ channels in guard cells play a role in light-induced stomatal opening in the presence of $Cs^+$, and that KAT1 functions as a plasma membrane $K^+_{in}$ channel in planta, these results were obtained with agents, i.e., pharmacological blockers, which can potentially affect multiple mechanisms in plant cells. For example, $Ba^{2+}$ blocks $K^+_{in}$ and outward-rectifying $K^+$ channels (Schroeder et al., 1987). Moreover, although 10 mM $Ba^{2+}$ blocks 90% of $K^+_{in}$ channel currents in faba bean guard cells (Schroeder et al., 1987), $Ba^{2+}$ does not affect the final stomatal apertures but affects only the rate of stomatal opening (Kelly et al., 1995). Further, several genetic loci in Arabidopsis affect $Cs^+$ sensitivity (Sheahan et al., 1993). Thus, the interpretation of pharmacological data relating to $K^+_{in}$ channels can be problematic.

Further, electrophysiological studies on guard cell $K^+$ channels have not been accompanied thus far by measurements of $K^+$ contents in guard cells to verify the proposed function of $K^+_{in}$ channels in $K^+$ uptake.

Thus, what is needed is a method to determine whether the specific inhibition of $K^+_{in}$ channel activity, e.g., in the absence of pharmacological blockers, is effective to inhibit light-induced stomatal guard cell opening in plants. What is also needed is a method which inhibits light-induced stomatal opening in a plant so as to increase drought tolerance in the plant.

SUMMARY OF THE INVENTION

The invention provides a method for increasing drought tolerance in a plant. The method comprises inhibiting or disabling $K^+_{in}$ channel activity in the stomatal guard cells of the plant, e.g., in a dicot or a monocot. $K^+_{in}$ channel activity may be measured by methods well known to the art including, but not limited to, $K^+$ uptake, e.g., into stomatal guard cells, $K^+$ currents, light-induced stomatal opening, final stomatal aperture diameter, or transpirational water loss from, for example, leaves of the plant. In one embodiment of the invention, the $K^+_{in}$ channel activity in the plant is inhibited or disabled by the expression of a DNA segment in the plant, e.g., a DNA segment which encodes a gene product that inhibits or reduces $K^+_{in}$ channel activity in the stomatal guard cells of the plant, for example, a gene product which interacts with a $K^+_{in}$ channel protein, e.g., a calcium-dependent protein kinase (Li et al., 1998) or protein phosphatase 2A (Li et al., 1994), and/or a gene product which encodes a $K^+$ channel protein. Thus, the plant may be a transgenic plant, the genome of which is augmented by a DNA segment such as one encoding an α or β subunit of a $K^+$ channel. Preferably, the DNA segment encodes a $K^+_{in}$ channel protein, e.g., KAT1 (Nakamura et al., 1995), KST1 (Müller-Röber et al., 1995), AKT1 or AKT2. Also preferably, the DNA segment comprises a gene, e.g., the KAT1 gene, with at least one dominant negative mutation.

As described hereinbelow, transgenic Arabidopsis plants were generated that expressed dominant negative point mutations in KAT1. Patch-clamp analyses with transgenic guard cells from two independent lines showed that $K^+_{in}$ peak currents were reduced by about 75% compared to controls at −180 mV, which resulted in significant inhibition of light-induced stomatal opening. Analysis of intracellular $K^+$ content with sodium hexanitrocobaltate (III) showed that $K^+$ uptake was also significantly reduced in guard cells of two strong suppressor lines during light-induced stomatal opening. Moreover, transpirational water loss from leaves was reduced. Interestingly, plant growth improved under limited watering conditions in these $K^+_{in}$ channel suppressor lines. Further, comparisons of guard cell $K^+_{in}$ current magnitudes among 4 different transgenic lines with different levels of expression of the dominant negative kat1 gene provided quantitative data on the range of activities of $K^+_{in}$ channels required for guard cell $K^+$ uptake during light-induced stomatal opening. These data provide molecular evidence that $K^+_{in}$ channels function as a major pathway for $K^+$ uptake in vivo during light-induced stomatal opening. Furthermore, quantitative data support the model that $K^+_{in}$ channel down-regulation during signal transduction, in parallel to regulation of H+ pumps, contributes to physiological stomatal regulation.

Thus, the invention also provides a method of preparing a plant that is drought tolerant. The method comprises introducing to plant cells an expression cassette comprising a DNA segment which encodes a gene product that inhibits or disables $K^+_{in}$ channel activity in stomatal guard cells so as to yield a transformed plant, the genome of which is augmented with the expression cassette. Then a transformed plant is identified which is tolerant to drought relative to a corresponding non-transformed plant. A preferred expression cassette for use in the method of the invention is an expression cassette comprising a nucleic acid segment which encodes a plant $K^+_{in}$ channel protein operably linked to a promoter functional in a plant cell. For example, the promoter may be a constitutive, strong promoter, e.g., a tandem repeat of the CaMV 35S promoter, an inducible promoter, for example, one which is induced by water deficiency, or a tissue specific promoter, i.e., one which is expressed in the guard cells of a plant. The nucleic acid segment of the expression cassette preferably comprises a plant $K^+_{in}$ channel protein gene which has at least one dominant negative mutation.

Thus, the invention further provides a plant having increased drought tolerance. The tolerance in the plant is due to inhibited or disabled $K^+_{in}$ channels in the guard cells of the plant. Preferred plants of the invention comprise a DNA segment that is expressed so as to suppress $K^+_{in}$ channel activity in the guard cells involved in stomatal opening. Preferred DNA segments encode a plant $K^+_{in}$ channel protein, e.g., one comprising at least one dominant negative mutation. Exemplary mutations are positioned in or near the pore region of a plant $K^+_{in}$ channel and/or in the voltage sensing region of a $K^+_{in}$ channel.

DETAILED DESCRIPTION OF THE INVENTION

Figure 1:
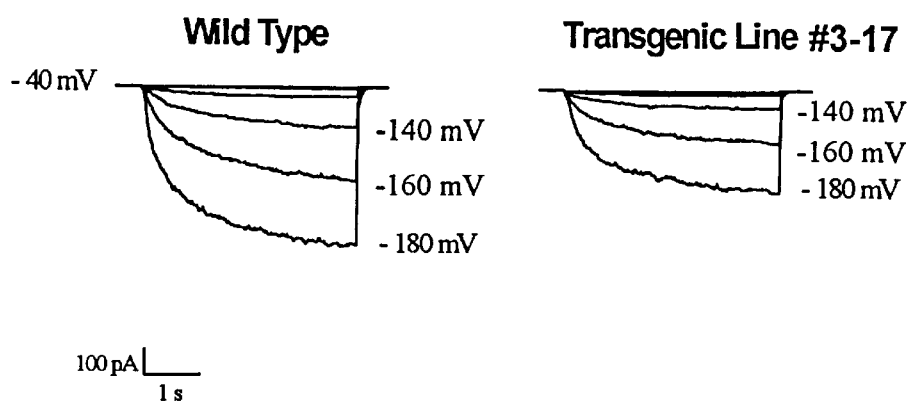
FIG. 1. Light-induced stomatal opening and reduced $K^+_{in}$ channel current magnitudes in transgenic line #3-17 in which a dominant negative KAT1 mutant is expressed under the control of a single CaMV 35S promoter. (A) Guard cell inward $K^+$ currents recorded from wild type (left) and transgenic line #3-17 (right) in the presence of 30 mM KCl. (B) Current-voltage curves plotted from whole-cell recordings of guard cells show an average 39% reduction in inward $K^+$ currents in transgenic guard cells (n=8, line #3-17) compared to wild-type controls (n=8). Membrane potentials were stepped from a holding potential of −40 mV to −180 mV in −20 mV increments. Data are mean ±SE. (C) Stomatal aperture before light exposure (solid bars; wild type). Stomata that were incubated for 2 hours in 1 mM KCl (crosshatched bars) or 10 mM KCl (open bars) do not show inhibition of light-induced stomatal opening. N=20 stomata for each condition. Error bars indicate SE.
Figure 1:
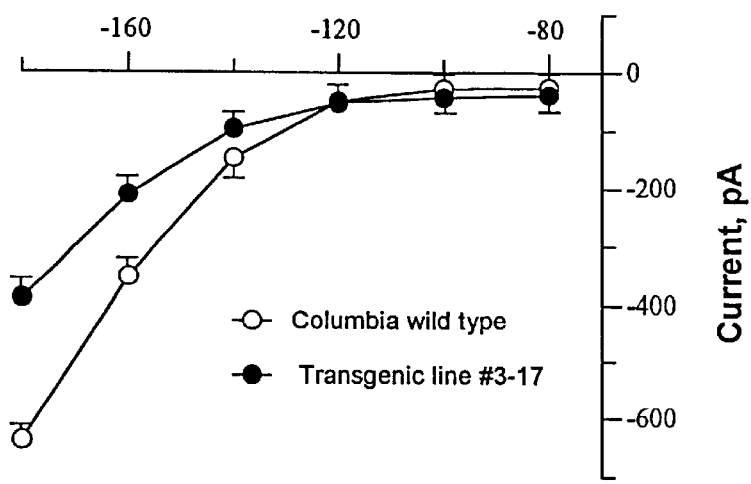
Figure 1:
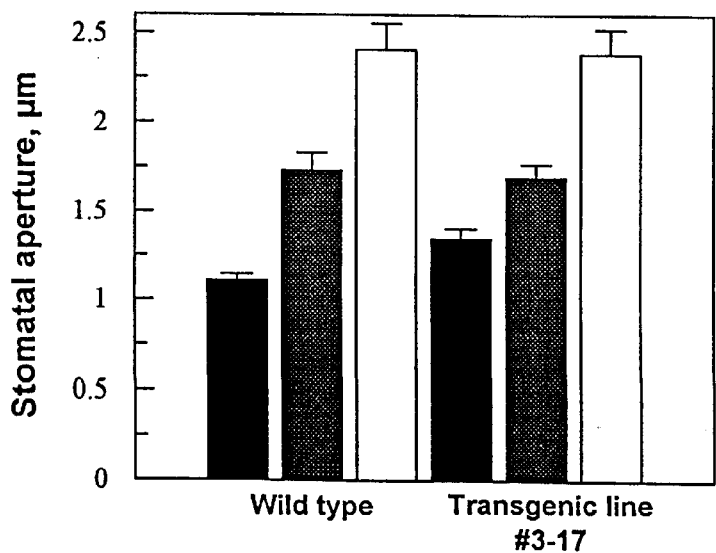

The identification and characterization of plants that are resistant or tolerant to water deprivation has long been a goal of agronomy. The manipulation and/or insertion of genes that can provide resistance or tolerance to water stress in plants has the potential for long term improvement in, and expansion of, agriculture worldwide. The method of the present invention, in which $K^+_{in}$ channel activity in the stomatal guard cells of a plant are inhibited or disabled, can be used with a variety of plants, and is especially useful for development of transgenic crop plants.

As used herein, "genetically modified" or "transgenic" means a plant cell, plant part, plant tissue or plant which comprises a preselected DNA segment or sequence which is introduced into a plant cell, plant part, plant tissue or plant, preferably into the genome of the plant cell, plant part, plant tissue or plant, by transformation. The term "wild type" refers to an untransformed plant cell, plant part, plant tissue or plant, i.e., one which has not been altered by the presence of the preselected DNA sequence.

As used herein, "plant" refers to either a whole plant, a plant tissue, a plant part, such as pollen or an embryo, a plant cell, or a group of plant cells. The class of plants which can be used in the method of the invention is generally as broad as the class of higher plants amenable to transformation techniques, including both monocotyledonous and dicotyledonous plants. The transformation of the plants in accordance with the invention may be carried out in essentially any of the various ways known to those skilled in the art of plant molecular biology. These include, but are not limited to, microprojectile bombardment, microinjection, electroporation of protoplasts or plant cells comprising partial cell walls, polyethylene-mediated transformation of protoplasts, silicon carbide-mediated transformation of intact plant cells, and Agrobacterium-mediated DNA transfer.

The terms "heterologous," "introduced," "foreign" or "transgenic" DNA or gene refer to a recombinant DNA segment, sequence or a gene that does not occur naturally in the genome of the plant that is the recipient of the recombinant DNA segment, sequence or gene, or that occurs in the recipient plant at a different location or association in the genome than in the untransformed plant.

As used herein, the terms "drought resistance" and "drought tolerance" are used to refer to a plant's increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of an isolated and purified DNA segment encoding a gene product that inhibits or disables $K^+_{in}$ channel activity in stomatal guard cells can impart protection against drought.

As used herein, the term "recipient cells" refers to cells that are receptive to transformation and subsequent regeneration into stably transformed, preferably fertile, plants and subsequent generation of stably transformed, fertile progeny plants. The plants are fertile in the sense that they can transmit the foreign DNA or transgenes through a complete sexual cycle to subsequent generations of progeny.

I. Recipient Cells

Recipient cell targets include, but are not limited to, callus, e.g., Type I, Type II, and Type III callus, suspension culture cells, protoplasts, leaf segments, stem segments, tassels, immature embryos and gametic cells such as microspores pollen, sperm and egg cells, hypocotyls, tuber segments, and meristematic regions, e.g., meristem cells. Type I, Type II, and Type III callus may be initiated from tissue sources including, but not limited to, immature embryos, seedling apical meristems, microspores and the like. Those cells which are capable of proliferating as callus are also recipient cells for genetic transformation. Any cell from which a fertile transgenic plant may be derived may be used as a recipient cell.

Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, and the like) may represent another type of recipient plant cell. Because of their undifferentiated growth and capacity for organ differentiation and totipotency, a single transformed meristematic cell could be recovered as a whole transformed plant. Embryogenic suspension cultures may be an in vitro meristematic cell system, retaining an ability for continued cell division in an undifferentiated state, controlled by the media environment.

Recipient cells may be somatic cells. Somatic cells are those cells of the plant which, during the normal course of development of the plant, do not contribute to the reproductive processes of the plant. Embryogenic cells are one example of somatic cells which may be induced in vivo to regenerate a plant through embryo formation.

Recipient cells can be selected following growth in culture. Cultured cells can be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components, the media differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells have been previously described.

Suitable recipient cultures can be initiated from a number of whole plant tissue explants including, but not limited to, immature embryos, leaf bases, immature tassels, anthers, microspores, and other tissues containing cells capable of in vitro proliferation and regeneration of fertile plants. Embryos produce callus that varies greatly in morphology, including those from highly unorganized cultures containing very early embryogenic structures (such as, but not limited to, type II cultures in maize), to those from highly organized cultures containing large late embryogenic structures (such as, but not limited to, type I cultures in maize). This variation in culture morphology may be related to genotype, culture medium composition, size of the initial embryos and other factors. Each of these types of culture morphologies can be a source of recipient cells.

The development of suspension cultures capable of plant regeneration may be used in conjunction with present invention. Suspension cultures can be initiated by transferring callus tissue to liquid culture medium containing growth regulators. Addition of coconut water or other substances to suspension culture medium may enhance growth and culture morphology, but the utility of suspension cultures is not limited to those containing these compounds. Suspension cultures can be preferred for generating progeny in the practice of the present invention, as these cultures grow more rapidly and are more easily manipulated than callus cells growing on solid culture medium.

When immature embryos or other tissues directly removed from a whole plant are used as the target tissue for DNA delivery, it is only necessary to initiate cultures of cells insofar as is necessary for identification and isolation of transformants. For example, DNA can be introduced by particle bombardment into immature embryos following their excision from the plant. Embryos can be transferred to a culture medium that will support proliferation of tissues and allow for selection of transformed sectors. Using this method, it is not necessary to establish stable callus cultures capable of long term maintenance and plant regeneration.

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all important factors in maintaining callus and/or suspension cultures that are useful as sources of recipient cells. Alternating callus between different culture conditions may be beneficial in enriching for recipient cells within a culture. For example, cells may be cultured in suspension culture, but transferred to solid medium at regular intervals. After a period of growth on solid medium cells can be manually selected for return to liquid culture medium. By repeating this sequence of transfers to fresh culture medium it is possible to enrich for recipient cells. Furthermore, passing cell cultures through a sieve, e.g., a 1.9 mm sieve, is useful in maintaining the friability of a callus or suspension culture and may be beneficial is enriching for transformable cells.

Additionally, cryopreservation may effect the development of, or perhaps select for, recipient cells. For use in transformation, suspension or callus culture cells can be cryopreserved and stored for periods of time, thawed, then used as recipient cells for transformation.

II. DNA Constructs of the Invention

The introduced DNA includes, but is not limited to, DNA from plant genes which encode gene products that inhibit or disable $K^+_{in}$ channel activity, e.g., either a $K^+$ channel gene or a non-$K^+$ channel gene, the product of which interacts directly or indirectly with a $K^+_{in}$ channel gene product. Preferably, the introduced DNA comprises a $K^+_{in}$ channel protein gene, and more preferably, a $K^+_{in}$ channel protein gene having at least one dominant negative mutation. The introduced DNA may also include non-plant genes such as those from bacteria, yeasts, animals or viruses. The introduced DNA can include modified genes, portions of genes, or chimeric genes, including genes from the same or different plant. The term "chimeric gene" or "chimeric DNA" is defined as a gene or DNA sequence or segment comprising at least two DNA sequences or segments from species which do not recombine DNA under natural conditions, or which DNA sequences or segments are positioned or linked in a manner which does not normally occur in the native genome of untransformed plant.

An isolated and purified DNA segment, molecule or sequence can be identified and isolated by standard methods, as described by Sambrook et al. (1989). The isolated and purified DNA segment can be identified by methods known to those of skill in the art.

A. Regulatory Sequences

Generally, the DNA is in the form of chimeric DNA, such as plasmid DNA, that can also contain coding regions flanked by regulatory sequences which promote the expression of the recombinant DNA present in the resultant plant (an "expression cassette"). For example, the DNA may itself comprise or consist of a promoter that is active in a plant which is derived from a non-plant source, or may utilize a promoter already present in the plant genotype.

Preferably, the expression cassette of the invention is operably linked to a promoter, which provides for expression of a linked DNA segment or sequence. The DNA segment or sequence is operably linked to the promoter when it is located downstream from the promoter, to form an expression cassette. An isolated promoter sequence that is a strong promoter for heterologous DNAs is advantageous because it provides for a sufficient level of gene expression to allow for easy detection and selection of transformed cells and provides for a high level of gene expression when desired.

Preferred expression cassettes will generally include a promoter which includes, but is not limited to, a strong constitutive promoter, such as the CaMV 35S promoter (Odell et al., *Nature,* 313, 810 (1985)), a tissue specific promoter, such a promoter which is preferentially expressed in guard cells, e.g., a $K^+_{in}$ channel protein gene promoter such as the KAT1 promoter, or an inducible promoter (e.g., a water-stress-, ABA- or turgor-inducible promoter, see Skriver et al., 1990). Other preferred promoters include the rab 18 (Lang et al., 1992) and rha1 (Terryn et al., 1993) promoters. Other promoters which direct specific or enhanced expression in certain plant tissues are known to those of skill in the art. Alternatively, novel tissue-specific promoter sequences may be employed in the practice of the invention.

A leader sequence can also be incorporated into the construct of the present invention. Preferred leader sequences include those which comprise sequences selected to direct optimum expression of the attached gene, i.e., to include a preferred consensus leader sequence which can increase or maintain MRNA stability and prevent inappropriate initiation of translation (Joshi, 1987). Such sequences are known to those of skill in the art. Sequences that are derived from genes that are highly expressed in plants are most preferred.

Regulatory elements such as Adh intron 1 (Callis et al., 1987), sucrose synthase intron (Vasil et al., 1989), rice actin 1 intron 1 (McElroy et al., 1991) or TMV omega element (Gallie et al., 1989) can also be included where desired. Other such regulatory elements useful in the practice of the invention are known to those of skill in the art.

An isolated and purified DNA segment can be combined with the transcription regulatory sequences by standard methods as described in Sambrook et al., cited supra, to yield an expression cassette. Briefly, a plasmid containing a promoter such as the 35S CaMV promoter can be constructed as described in Jefferson (1987) or obtained from Clontech Lab in Palo Alto, Calif. (e.g., pBI121 or pBI221). Typically, these plasmids are constructed to provide for multiple cloning sites having specificity for different restriction enzymes downstream from the promoter. The isolated and purified DNA segment can be subcloned downstream from the promoter using restriction enzymes to ensure that the DNA is inserted in proper orientation with respect to the promoter so that the DNA can be expressed. Once the isolated and purified DNA segment is operably linked to a promoter, the expression cassette so formed can be subcloned into a plasmid or other vectors.

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. Preferred 3' elements are derived from those from the nopaline synthase gene of *Agrobacterium tumefaciens* (Bevan et al., 1983), the terminator for the T7 transcript from the *Agrobacterium tumefaciens*, T-DNA and the 3' end of the protease inhibitor I or II genes from potato or tomato, although other 3' elements known to those of skill in the art can also be employed. These 3' nontranslated regulatory sequences can be obtained as described in *Methods in Enzymology*, 153, 292 (1987) or are already present in plasmids available from commercial sources such as Clontech (Palo Alto, Calif.). The 3' nontranslated regulatory sequences can be operably linked to the 3' terminus of the isolated and purified DNA segment by standard methods.

B. Marker Genes

In order to improve the ability to identify transformants, one may desire to employ one or more selectable marker genes or reporter genes as, or in addition to, the expressible isolated and purified DNA segment(s). "Marker genes" or "reporter genes" are genes that impart a distinct phenotype to cells expressing the marker gene and thus allow such transformed cells to be distinguished from cells that do not have the gene. Such genes may encode either a selectable or screenable marker, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Of course, many examples of suitable marker genes or reporter genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall.

Possible selectable markers for use in connection with the present invention include, but are not limited to, a neo gene (Potrykus et al., 1985) which codes for kanamycin resistance and can be selected for using kanamycin, G418, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) or acetoacid synthase gene (AAS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon (U.S. Pat. No. 5,780,708); or a mutated anthranilate synthase gene that confers resistance to 5-methyl tryptophan (PCT Pub. No. WO 97/26366). Where a mutant EPSP synthase gene is employed, additional benefit may be realized through the incorporation of a suitable chloroplast transit peptide, CTP (U.S. Pat. No. 4,940,835). See also, Lundquist et al., U.S. Pat. No. 5,508,468.

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase (Murakami et al., 1986; Twell et al., 1989) causing rapid accumulation of ammonia and cell death.

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

C. Other Sequences

An expression cassette of the invention can also be further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti vector can be replicated in prokaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the co/E1 replication of origin and a wide host range replicon. The binary Ti vectors carrying an expression cassette of the invention can be used to transform both prokaryotic and eukaryotic cells, but is preferably used to transform plant cells.

In certain embodiments, it is contemplated that one may wish to employ replication-competent viral vectors in transformation. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu may actively promote integration of the desired DNA and hence increase the frequency of stably transformed cells.

Vectors, plasmids, cosmids, YACs (yeast artificial chromosomes) and DNA segments for use in transforming such cells will, of course, generally comprise the isolated and purified cDNA(s), isolated and purified DNA(s) or genes which one desires to introduce into the cells. These DNA constructs can further include structures such as promoters, enhancers, polylinkers, or even regulatory genes as desired. The DNA segment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

III. DNA Delivery of DNA Molecules to Host Cells

The present invention generally includes steps directed to introducing an isolated and purified DNA segment or sequence, such as an isolated and purified cDNA, into a recipient cell to create a transformed cell. It is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants.

Cells of the plant tissue source are preferably embryogenic cells or cell-lines that can regenerate fertile transgenic plants and/or seeds. The cells can be derived from either monocotyledons or dicotyledons. Suitable examples of plant species include wheat, rice, Arabidopsis, tobacco, maize, soybean, and the like.

Transformation of the cells of the plant tissue source can be conducted by any one of a number of methods known to those of skill in the art. Examples are: agitation of cells with DNA in the presence of metal or ceramic whiskers (U.S. Pat. No. 5,302,523); transformation by direct DNA transfer into plant cells by electroporation (U.S. Pat. Nos. 5,384,253 and 5,472,869; Dekeyser et al., 1990); direct DNA transfer to plant cells by PEG precipitation (Hayashimoto et al., 1990); direct DNA transfer to plant cells by microprojectile bombardment (McCabe et al., 1988); Gordon-Kamm et al., 1990); U.S. Pat. Nos. 5,489,520; 5,538,877; and 5,538,880) and DNA transfer to plant cells via infection with Agrobacterium. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction. See also, R. Chasan (1992).

A preferred method for dicot transformation is via infection of plant cells with *Agrobacterium tumefaciens* using the leaf-disk protocol (Horsch et al., 1985). Methods for transformation of monocotyledonous plants utilizing *Agrobacterium tumefaciens* have been described by Hiei et al. (U.S. Pat. No. 5,591,616) and Saito et al. (European Patent No. 0 672 752).

An expression cassette of the invention can be introduced by methods of transformation, for example, methods which are especially effective for monocots, including, but not limited to, microprojectile bombardment of immature embryos or embryogenic callus cells, or by electroporation of embryogenic calluses.

The choice of plant tissue source for transformation will depend on the nature of the host plant and the transformation protocol. The tissue source is selected and transformed so that it retains the ability to regenerate whole, fertile plants following transformation, i.e., contains totipotent cells.

The transformation is carried out under conditions directed to the plant tissue of choice. The plant cells or tissue are exposed to the DNA carrying the isolated and purified DNA sequences for an effective period of time. This may range from a less-than-one-second pulse of electricity for electroporation to a 2–3 day co-cultivation in the presence of plasmid-bearing Agrobacterium cells. Buffers and media used will also vary with the plant tissue source and transformation protocol. Many transformation protocols employ a feeder layer of suspension culture cells (tobacco or Black Mexican Sweet corn, for example) on the surface of solid media plates, separated by a sterile filter disk from the plant cells or tissues being transformed.

IV. Production and Characterization of Stable Transgenic Plants

After effecting delivery of an isolated and purified DNA segment or sequence to recipient cells by any of the methods discussed above, the next steps of the invention generally concern identifying the transformed cells for further culturing and plant regeneration. As mentioned above, in order to improve the ability to identify transformants, one may desire to employ a selectable or screenable marker gene as, or in addition to, the expressible isolated and purified DNA segment or sequence. In this case, one would then generally assay the potentially transformed cell population by exposing the cells to a selective agent or agents, or one would screen the cells for the desired marker gene trait.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the isolated and purified DNA segment into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced isolated and purified DNA segment, the plant is self-pollinated at least once in order to produce a homozygous backcross converted inbred containing the isolated and purified DNA segment. Progeny of these plants are true breeding.

Alternatively, seed from transformed plants regenerated from transformed tissue cultures is grown in the field and self-pollinated to generate true breeding plants. Progenies from these plants become true breeding lines which are evaluated for a desired phenotype or trait.

Upon the identification of the superior performance of transgenic plants, the parent selections are advanced and inbred lines are produced through conventional breeding techniques. Hybrid plants having one or more parents containing the isolated and purified DNA segment are tested in commercial testing and evaluation programs and performance documented.

A. Characterization

To confirm the presence of the isolated and purified DNA segment(s) or "transgene(s)" in the regenerating plants, a variety of assays may be performed. Such assays include, for example, "molecular biological" assays well known to those of skill in the art, such as Southern and Northern blotting, RT-PCR and PCR; "biochemical" assays, such as detecting the presence of a protein product, e.g., by immunological means (ELISAs and Western blots) or by enzymatic function; plant part assays, such as stomatal aperture assays; and also, by analyzing the phenotype of the whole regenerated plant, e.g., for drought resistance.

1. DNA Integration, RNA Expression and Inheritance

Genomic DNA may be isolated from callus cell lines or any plant parts to determine the presence of the isolated and purified DNA segment through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique discreet fragments of DNA are amplified and detected by gel electrophoresis. This type of analysis permits one to determine whether an isolated and purified DNA segment is present in a stable transformant, but does not prove integration of the introduced isolated and purified DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced isolated and purified DNA segment.

Positive proof of DNA integration into the host genome and the independent identities of transform ants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced isolated and purified DNA segments in high molecular weight DNA, i.e., confirm that the introduced isolated and purified DNA segment has been integrated into the host cell genome. The technique of Southern hybridization provides information that is obtained using PCR, e.g., the presence of an isolated and purified DNA segment, but also demonstrates integration into the genome and characterizes each individual transform ant.

It is contemplated that using the techniques of dot or slot blot hybridization which are modifications of Southern hybridization techniques one could obtain the same information that is derived from PCR, e.g., the presence of an isolated and purified DNA segment. However, it is well known in the art that dot or slot blot hybridization may produce misleading results, as probe may be non-specifically bound by high molecular weight DNA.

Both PCR and Southern hybridization techniques can be used to demonstrate transmission of an isolated and purified DNA segment to progeny. In most instances the characteristic Southern hybridization pattern for a given transformant will segregate in progeny as one or more Mendelian genes (Spencer et al., 1992; Laursen et al., 1994) indicating stable inheritance of the gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced isolated and purified DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

2. Gene Expression

While Southern blotting and PCR may be used to detect the isolated and purified DNA segment in question, they do not provide information as to whether the isolated and purified DNA segment is being expressed. Expression may be evaluated by specifically identifying the protein products of the introduced isolated and purified DNA segments or evaluating the phenotypic changes brought about by their expression.

Assays for the production and identification of specific proteins and the levels thereof may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins offer opportunities for use of specific antibodies to detect their presence in formats such as an immunoassay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures.

Very frequently the expression of a gene product is determined by evaluating the phenotypic results of its expression. These assays also may take many forms including but not limited to analyzing changes in the chemical composition, morphology, or physiological properties of the plant. Most often changes in response of plants or plant parts to imposed treatments are evaluated under carefully controlled conditions termed bioassays.

The invention will be further described by the following non-limiting example.

EXAMPLE 1

Materials and Methods

Plant Transformation

Two dominant negative KAT1 mutants which have a point mutation at either amino acid 256 (T256R) and/or at 262 (G262K) (Baizabal-Aguirre et al., 1999) were subcloned into plant expression vectors (pBIN-JIT) containing a tandem repeat of cauliflower mosaic virus 35S promoter (a gift from Dr. Cathie Martin, John Innes Center, UK) and the pMON530 vector (Monsanto, St. Louis, Mo.). Two vectors and the two resulting constructs, pKAT1-T256R and pKAT1-G262K, either in pBIN-JIT or in pMON530, were introduced into *Agrobacterium tumefaciens* C58 strain and the resulting strains were used to transform *Arabidopsis thaliana* ecotype Columbia (Col-O) by the vacuum infiltration method (Bechtold et al., 1993).

RNA Blot Analysis

Total cellular RNA was extracted from Arabidopsis leaves using Trizol reagent (Life Technologies, Rockville, Md.). Twenty-five micrograms of RNA was separated on a denaturing 1.2% agarose gel and then transferred onto a Hybond-N nylon membrane (Amersham). The blot was hybridized and washed as described in Kwak et al. (1997). RNA loading was assessed by probing the blot with an 18S rRNA gene of *Brassica napus* (Park et al., 1993).

Stomatal Aperture, Transpirational Water Loss and Plant Growth Measurements

Stomatal aperture measurements were performed as described in Ichida et al. (1997) with a slight modification. Fully expanded rosette leaves from 4-week old plants were detached and floated in water in darkness overnight to induce stomatal closing. One or two leaves were then transferred and submerged in stomatal opening solution (30 mM KCl, 0.1 mM $CaCl_2$, 10 mM Mes-KOH, pH 6.15) and incubated under white light with a fluence rate of 150 mmol $m^{-2}$ $sec^{-1}$ for 3 hours.

Transgenic lines that showed inhibition of light-induced stomatal opening in the T1 generation were selected by measuring 16 to 20 stomata from each independent plant. In the T2 generation, 2 plants per transgenic line were chosen and 20 stomata were assayed for each plant. To analyze light-induced stomatal opening of homozygous transgenic $K^+_{in}$ suppressor lines and control plants, 20 stomata were measured for each time point and measurements were repeated several times for each line.

Measurements of transpirational water loss in detached rosette leaves of transgenic $K^+_{in}$ suppressor lines, control, and abi1-1 mutant plants were performed as described in Hong et al. (1997). In each experiment, 3 leaves per plant were used and 3 independent experiments were conducted. To analyze plant growth under dehydrated conditions, plants were watered every 7 or 8 days with about 30 ml per pot from 12 days after germination, whereas, under normal watering conditions, plants were watered every 3 days with about 30 ml per pot. At 26 and 34 days after germination, fresh weights of $6^{th}$ and $7^{th}$ leaves were measured. In each experiment, 3 plants were used and 2 independent experiments were performed.

Patch-Clamp Analyses

*A. thaliana* guard cell protoplasts were enzymatically isolated from rosette leaves of 4–6 week old plants, as previously described (Pei et al., 1997). Epidermal strips were incubated in 10 ml of medium containing 1% cellulase R10 and 0.5% macerozyme R10 (Yakult Honsha, Tokyo), 0.1 mM KCl, 0.1 mM $CaCl_2$, 500 mM D-mannitol, 0.5% BSA, 0.1% kanamycin sulfate, and 10 mM ascorbic acid-Tris (pH 5.5) for 16 hours at 25° C. Isolated protoplasts were stored on ice and used directly after isolation. Whole-cell recordings of Arabidopsis guard cells were performed as described in Tchida et al. (1997). The pipette solution was composed of 30 mM KCl, 70 mM K-glutamate, 2 mM $MgCl_2$, 6.7 mM EGTA, 3.35 mM $CaCl_2$, 5 mM ATP and 10 mM HEPES-Tris (pH 7.1). The bath solution contained 30 mM KCl, 40 mM $CaCl_2$, 2 mM $MgCl_2$ and 10 mM MES-Tris (pH 5.5). Osmolalities of all solutions were adjusted to 500 mmol/kg for pipette solutions and 485 mmol/kg for bath solutions by the addition of D-sorbitol. The voltage protocol stepped the voltage from a holding potential of −40 mV to −180 mV in −20 mV increments. Any leak currents were not subtracted.

Determination of Relative Intracellular Potassium Ion Content

To close stomata, rosette leaves were detached from 4–6 weeks old plants and incubated in a solution containing 5 mM KCl and 1 mM $CaCl_2$ overnight at 22° C. in the dark. To induce stomatal opening, the leaves were floated in the same solution for 30 minutes at 22° C. in white light in a solution containing 5 mM KCl and 1 mM $CaCl_2$. At each time point, leaf epidermis were manually peeled under deionized water and then the epidermal peels were stained with freshly prepared 0.5 M sodium hexanitrocobaltate (III) (SHC) in 10% (v/v) acetic acid (Green et al., 1990). Intracellular $K^+$ precipitate granules produced by SHC treatment were scored with a Nikon Diaphot 300 microscope and NIH image software. In brief, stained stomatal images were stored and then a fixed brightness threshold was selected to convert stomatal images to pixels. Stained $K^+$ granules were scored by counting pixels after manual removal of noise pixels which were not within the outline of guard cells. Data analyses were performed using Microsoft Excel software (version 98, Microsoft Corporation, Redwood, Calif.).

Results

Transgenic Arabidopsis plants were prepared that express dominant negative KAT1 mutants containing point mutations in the pore region of KAT1. A previous study has shown that two point mutations in the pore region of KAT1 (T256R and G262K) function as dominant negative KAT1 mutations in situ (Baizabal-Aguirre et al., 1999). Coexpression of either one of these mutants together with wild-type KAT1 suppressed in $K^+_{in}$ currents in Xenopus oocytes (Baizabal-Aguirre et al., 1999).

Partial Suppression of $K^+_{in}$ Channel Activity

To investigate the suggested role of $K^+_{in}$ channels in stomatal opening in vivo, transgenic Arabidopsis plants were generated which express the dominant negative mutant kat1-T256R under control of a single CaMV 35S promoter. Nine single-insertion homozygous T2 plants that showed transgene expression, based on Northern blot analysis, were selected. Transgenic guard cells from 9 transgenic lines were patch clamped to measure $K^+_{in}$ currents and 6 independent lines showed similar reduction in $K^+_{in}$ currents. Of six transgenic lines, one transgenic line was selected (line #3-17) to analyze its phenotype in detail. As shown in FIGS. 1A and 1B, the magnitude of $K^+_{in}$ currents was reduced in guard cells of transgenic line #3-17 by 39% (n=8) at −180 mV compared to wild-type controls (n=8). Northern blot analyses confirmed the expression of the kat1-T256R transgene. However, light-induced stomatal opening was not affected in transgenic guard cells (n=20) when epidermal peels were incubated for 2 hours in white light (FIG. 1C), suggesting that the reduction in $K^+_{in}$ currents in these transgenic guard cells did not affect light-induced stomatal opening (P<0.01, 10 mM KCl in the stomatal opening solution, FIG. 1C, open bars). Moreover, when extracellular $K^+$ was reduced to 1 mM, $K^+_{in}$ channel suppression also did not affect light-induced stomatal opening (FIG. 1C, gray bars, P<0.05).

Overexpression of Dominant Negative KAT1 Mutants Inhibits Light-Induced Stomatal Opening Subsequently, a plant expression vector was used that contains a tandem-repeat of the CaMV 35S promoter to increase the level of expression of dominant negative KAT1 mutants. Two previously characterized dominant negative $K^+_{in}$ channel mutants, kat1-T256R and kat1-G262K (Baizabal-Aguirre et al., 1999) were expressed under the control of this promoter. Nineteen transgenic Arabidopsis lines expressing kat1-T256R and 12 lines expressing kat1-G262K were generated. Light-induced stomatal opening was examined following transformation of all lines.

Preliminary stomatal aperture measurements on the 31 transgenic lines (2 plants analyzed per line) in the T1 generation led to identification of 12 transgenic lines which showed reduced stomatal opening. Among these, 9 transgenic repressor lines were selected that showed a Mendelian segregation ratio of 3:1 for kanamycin resistance in the T2 generation indicating a single T-DNA insertion in the genome. For each line, two plants were analyzed per generation. Of these lines, two transgenic $K^+_{in}$ suppressor lines (kat1-T256R line #15-4 and #22-6) were selected for detailed analysis. Both lines showed a reproducible and significant inhibition of light-induced stomatal opening in stomatal aperture measurements in subsequent generations. Homozygous offspring (T3 generation) of these two lines with a single T-DNA insertion were isolated. Another homozygous transgenic line was chosen (kat1-T256R #23-4) which did not show inhibition of light-induced stomatal opening for control experiments.

Epidermal peels from plants were incubated in a stomatal opening solution for 3 hours in white light. As shown in FIG. 2A, stomata of the two transgenic $K^+_{in}$ suppressor lines, #15-4 and #22-6, did not open widely in response to white light compared to vector-transformed controls (P<0.005, #15-4: P<0.003, #22-6) and the transgenic control line #23-4 (P<0.002, #15-4; P<0.0001, #22-6). Furthermore, prior to light exposure, stomatal apertures were significantly smaller in the #15-4 line (P<0.023) and the #22-6 line (P<0.01) compared to vector-transformed controls (FIG. 2A). Stomatal apertures in vector-transformed control plants were enhanced by light by an average of 77% (FIG. 2A, left). Furthermore, stomatal apertures increased by an average of 85% in the control line #23-4 (FIG. 2A, right). In contrast, stomatal apertures increased in the kat1-T256R line #15-4 in the light by an average of only 29% and in line #22-6 by an average of 35%. Interestingly, stomatal apertures after 3 hours light exposure in both suppressor lines barely reached levels of those for dark-treated control plants (FIG. 2A).

To examine KAT1 mutant expression in transgenic Arabidopsis plants, RNA blot analyses were performed. As shown in FIG. 2B, the transgenic KAT1 transcript was detected in all 3 transgenic $K^+_{in}$ suppressor lines. In contrast, KAT1 transcript was not detected in vector-transformed control plants as previously reported (Ichida et al., 1997; Coo et al., 1995) due to preferential expression of KAT1 in guard cells (FIG. 2B) (Nakamura et al., 1995). To determine the relative amounts of RNA samples loaded, the blot was hybridized with an 18S rDNA probe (FIG. 2C). The control line #23-4 showed lower transgene expression levels than lines #15-4 and #22-6 (FIGS. 2B and 2C).

Guard Cells From Transgenic Arabidopsis Plants Showing Inhibition of Light-Induced Stomatal Opening Have Significantly Reduced $K^+_{in}$ Currents The differences in light-induced stomatal opening prompted the examination of the activities of guard cell $K^+_{in}$ channels of Columbia wild-type, vector-transformed control plants and the three transgenic $K^+_{in}$ suppressor lines. As shown in FIGS. 3A and 3B, hyperpolarization of Arabidopsis guard cells activated $K^+_{in}$ currents in wild-type and control plants. The average steady-state whole-cell currents at −180 mV were −440.3±73.0 pA (n=11) for wild-type Columbia and −398.5±104.8 pA (n=6) for control plants (FIGS. 3A and 3B), showing that control transformation did not significantly affect $K^+_{in}$ currents in guard cells (P>0.74). $K^+_{in}$ channels were activated by hyperpolarization of guard cells from transgenic $K^+_{in}$ suppressor lines #15-4 and #22-6, however, the magnitudes of $K^+_{in}$ currents were significantly reduced compared to wild-type and control plants (FIGS. 3C and 3D; P<0.01). The average steady-state whole-cell current at −180 mV in line #15-4 was −106.9±16.2 pA (FIG. 3C; 73.2% reduction compared to controls, n=14) and −100.2±18.7 pA in line #22-6 (FIG. 3D; 74.9% reduction compared to controls, n=10). In the transgenic line #23-4 which did not show a clear reduction in light-induced stomatal opening (FIG. 2A, right), $K^+_{in}$ currents were reduced by 57.8% (FIG. 3E; −168.0±27.6 pA at −180 mV, n=5). Together with data shown in FIG. 1, these results suggest that reduction in $K^+_{in}$ channel activity by 58% or less in guard cells still allows light-induced stomatal opening but a reduction by 75% reduces light-induced stomatal opening.

Figure 4:
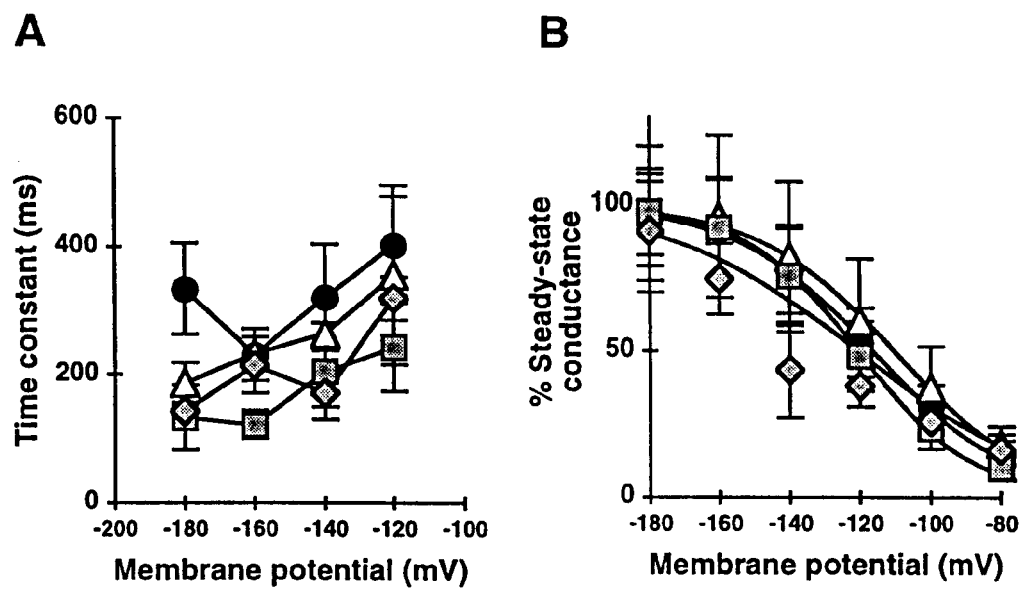
FIG. 4. Comparison of activation times and steady-state chord conductance of inward $K^+$ currents in the transgenic $K^+_{in}$ channel suppressor lines, vector-transformed control and wild-type plants. (A) The activation time constant of inward $K^+$ currents was plotted as a function of the membrane potential. Error bars indicate SE. (B) Steady-state chord conductance curves were plotted as a function of the membrane potential. Solid lines represent Boltzman fits. Error bars are SE. Wild type data (filled circles, n=11), vector-transformed controls (open triangles, n=5) and transgenic $K^+_{in}$ channel suppressor lines #15-4 (gray rectangles, n=14) and #22-6 (gray diamonds, n=10).

The activation times and chord conductances of $K^+_{in}$ channel currents were analyzed to determine whether physiological properties of $K^+_{in}$ channels are changed in the strong transgenic $K^+_{in}$ channel suppressor lines. Activation of inward-rectifying $K^+$ currents was fitted by single-exponential functions. As shown in FIG. 4A, activation time constants showed only weak voltage dependence at membrane potentials from −120 to −160 mV in all plant lines examined and there were no significant differences among plant lines. The steady-state chord conductance was analyzed as a function of membrane potential (FIG. 4B) to determine whether inward-rectifying current activation is affected by dominant negative KAT1 mutations. Half-maximal activation potentials were similar although slightly more negative in cells containing the dominant negative KAT1 mutants (FIG. 4B).

$K^+_{in}$ Channel Activity Suppression Reduces Transpirational Water Loss

Figure 5:
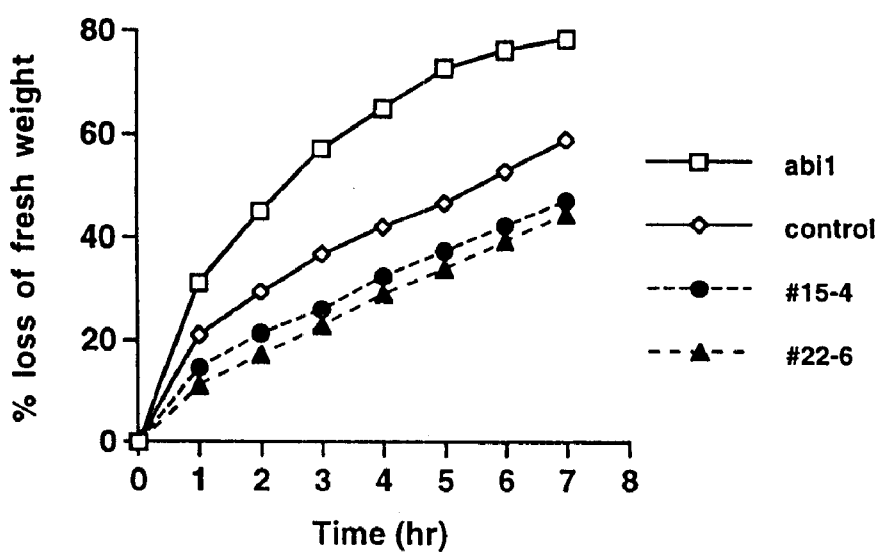
FIG. 5. Time course measurements of transpirational water loss show that suppression of $K^+_{in}$ channel activity causes less water loss in detached leaves of transgenic $K^+_{in}$ channel suppressor lines #15-4 and #22-6 than in vector-transformed controls. For comparison, the abi1-1 mutant was used in parallel. Data show a representative result of 3 independent measurements. In each experiment, fresh weights of 3 leaves per plant were measured under 10% humidity conditions.

To determine whether reduction in light-induced stomatal opening affects transpirational water loss from leaves, water loss rates of detached leaves of transgenic $K^+_{in}$ channel suppressor lines were measured. During 7 hour measurements, detached leaves of both of the $K^+_{in}$ channel suppressor lines #15-4 and #22-6 consistently lost less water than control leaves (FIG. 5; P<0.01, in 3 experiments). The ABA-insensitive mutant abi1-1 was analyzed in parallel for relative comparison to control and transgenic lines. Fifty percent of fresh weight loss was observed after 2 to 3 hours in 10% air humidity from detached leaves of abi1-1 mutant plants and almost 80% loss of fresh weight was observed for abi1-1 after 7 hours (FIG. 5). After 7 hours, control leaves lost approximately 60% of fresh weight (FIG. 5). In contrast, only about 45% (47% loss in #15-4 and 44% loss in #22-6) of fresh weight was lost in leaves from both of the two transgenic $K^+_{in}$ suppressor lines, showing that expression of dominant negative KAT1 mutants causes reduced water loss from leaves of transgenic $K^+_{in}$ suppressor lines which correlates with the observed reduction in stomatal apertures in both light- and dark-treated leaves (FIG. 2A).

Figure 6:
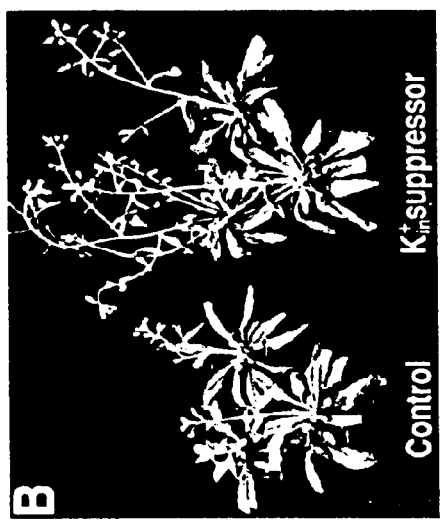
FIG. 6. Transgenic $K^+_{in}$ channel suppressor lines show an enhanced growth compared to control plants under reduced watering conditions. (A, B) Both vector-transformed controls (left in A and B) and transgenic $K^+_{in}$ channel suppressor line #15-4 (right in A and B) were grown under well-watered (A) and reduced watering conditions (B). Pictures were taken 34 days after germination. (C, D) Fresh weights of $6^{th}$ or $7^{th}$ leaves of plants that were grown under well-watered (C) and reduced watering conditions (D) were measured 34 days after germination. Well-watered corresponds to watering every 3 days and reduced watering to every 7 to 8 days. Error bars show SE.
Figure 6:
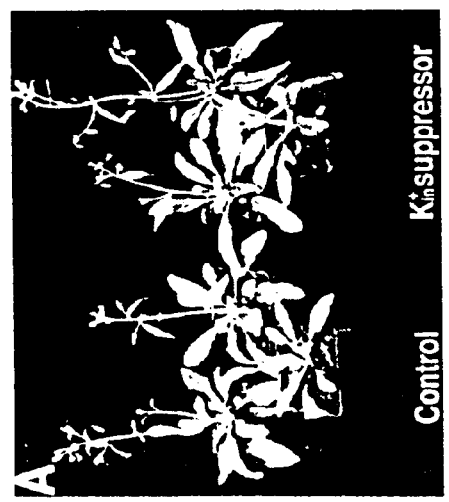
Figure 6:
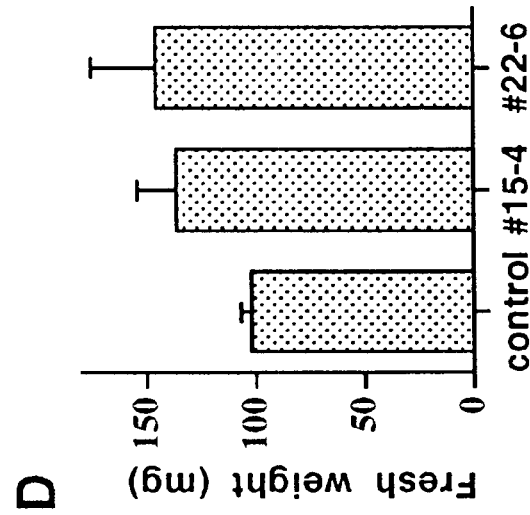
Figure 6:
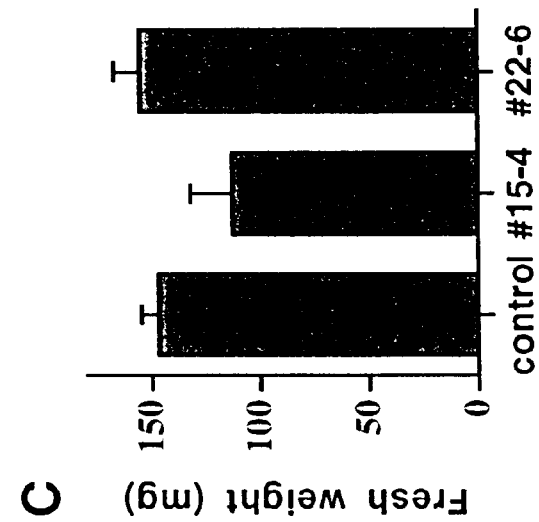

Experiments were pursued to determine whether $K^+_{in}$ current reduction affected plant growth. Growth of both controls and the transgenic $K^+_{in}$ suppressor lines was similar under well-watered conditions (FIG. 6A). Interestingly however, the two transgenic $K^+_{in}$ suppressor lines showed a reproducible enhancement in growth compared to vector-transformed control plants when plants were subjected to reduced watering conditions (FIG. 6B). Fresh weights of total aerial tissue were increased by 42% in line #15-4 (P<0.05) and 39% in line #22-6 (P<0.05) 41 days after germination. Furthermore, $K^+_{in}$ channel suppression increased fresh weights of leaves when water supply was limited. Fresh weights of $6^{th}$ or $7^{th}$ leaves of the transgenic $K^+_{in}$ suppressor lines increased from 34 to 43% compared to vector-transformed controls at 34 days after germination (FIG. 6D; 34% increase for line #15-4, P<0.01; 43% increase of line #22-6, P<0.05). A similar extent of growth and fresh weight enhancement in the transgenic lines was also observed 26 days after germination (data not shown). When plants were watered well, fresh weights of leaves did not significantly increase in transgenic $K^+_{in}$ suppressor lines compared to controls (FIG. 6C).

Reduced $K^+$ Uptake in Transgenic Guard Cells

Results from stomatal aperture measurements, patch clamp analyses, transpiration rate measurements and fresh weight analyses suggest that dominant negative KAT1 mutants may cause reduced $K^+$ uptake in transgenic guard cells. To determine whether the dominant negative kat1-T256R mutants reduce $K^+$ uptake during light-induced stomatal opening, epidermal strips were stained with sodium hexanitrocobaltate (III) (SHC) which is a $K^+$ specific stain and produces $K^+$ granules in guard cells (Green et al., 1990). Staining was then semi-quantitatively analyzed in stomata from several plants to measure relative intracellular $K^+$ contents in guard cells before and after exposure to light from wild-type, control and transgenic $K^+_{in}$ suppressor lines using digital image analyses.

Figure 7:
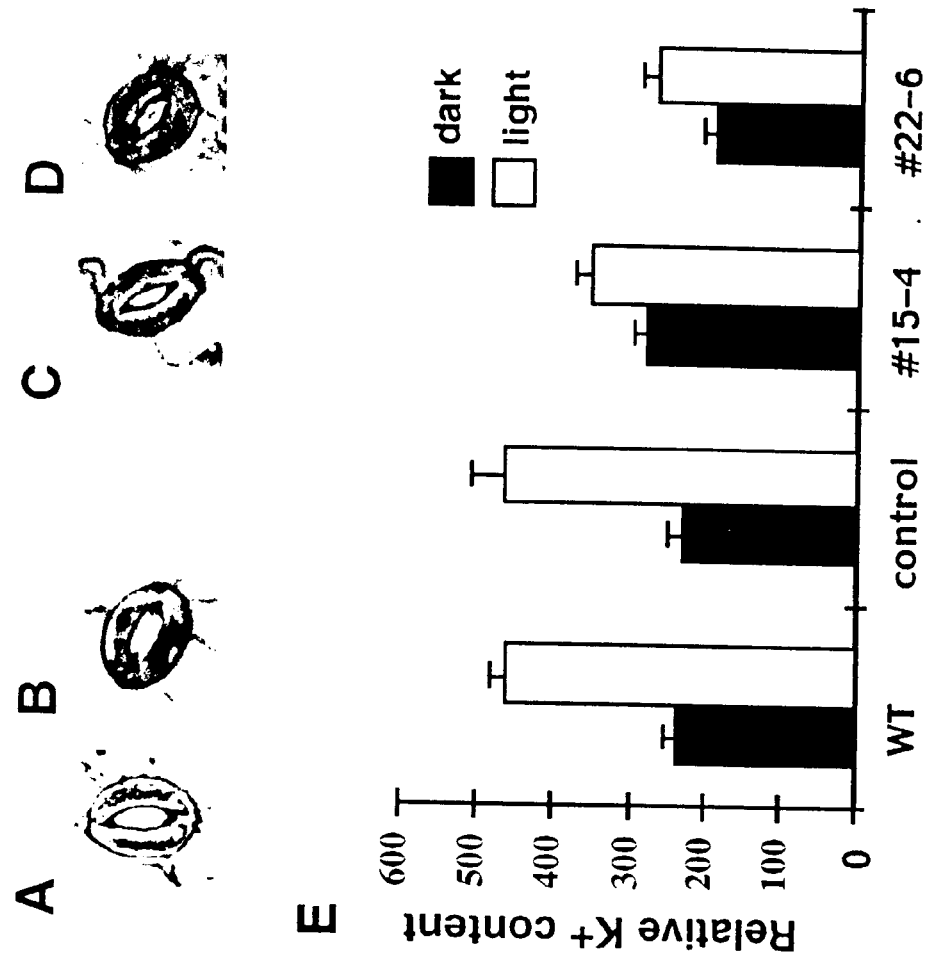
FIG. 7. Analysis of intracellular $K^+$ content shows that suppression of $K^+_{in}$ channel activity reduces $K^+$ uptake in guard cells of transgenic $K^+_{in}$ channel suppressor lines #15-4 and #22-6 during light-induced stomatal opening. Examples of sodium hexanitrocobaltate (III) stained Arabidopsis stomatal complex from wild-type Arabidopsis before (A) and after (B) light incubation for 30 minutes. Examples of sodium hexanitrocobaltate (III) stained Arabidopsis stomatal complexes from transgenic $K^+_{in}$ channel suppressor line #22-6 before (C) and after (D) light incubation for 30 minutes. (E) Relative intracellular $K^+$ content in guard cells of wild type (n=60 stomata before and 35 stomata after light incubation), vector-transformed control (n=61 stomata before and after light incubation), and transgenic $K^+_{in}$ channel suppressor lines #15-4 (n=61 stomata before and 71 stomata after light incubation) and #22-6 (n=49 stomata before and after light incubation). Solid bar and open bar represent before and after light incubation, respectively. Error bars show SE.

FIG. 7 shows typical $K^+$ staining in Arabidopsis guard cells before (FIG. 7A) and after (FIG. 7B) exposure to light. Before light exposure, the cells had a low $K^+$ content as demonstrated by a lack of substantial staining (FIGS. 7A and 7C). After 30 minutes of light exposure, dark $K^+$ granules were observed that label cellular $K^+$ in wild-type guard cells (FIG. 7B) (Green et al., 1990). In transgenic $K^+_{in}$ suppressor lines (FIG. 7D), $K^+$ granules were consistently less pronounced after 30 minutes light exposure than in wild-type controls. Note that clear differences in stomatal apertures were not observed following staining because acetic acid treatment during the staining procedure reduces apertures (FIGS. 7B and 7D) (Green et al., 1990).

Analysis of data from all experiments showed that light-induced stomatal opening caused a twofold increase in the relative $K^+$-dependent staining in vector-transformed control (n=61 stomata before and 61 after light incubation) and wild-type guard cells (n=60 stomata before and 35 stomata after light incubation) (FIG. 7E, wt and control). In contrast, the intracellular $K^+$ content was increased by only 26.5% in guard cells of transgenic line #15-4 (n=61 stomata before and 71 stomata after light incubation) and by 41% in guard cells of line #22-6 (n=49 stomata before and 49 after light incubation; FIG. 7E). These data show that $K^+$ accumulation in guard cells of transgenic lines #15-4 and #22-6 was significantly reduced compared to wild-type and control guard cells (P<0.01). These data provide molecular evidence that guard cell $K^+_{in}$ channels function as a pathway for $K^+$ uptake in vivo during light-induced stomatal opening and provide direct information on $K^+_{in}$ channel activity levels that become limiting under physiological conditions.

Discussion $K^+_{in}$ channels in the plasma membrane of plant cells have been proposed to be important for mediating $K^+$ uptake into various plant cell types. Two insertional disruption mutants in Arabidopsis root $K^+$ channel genes have been reported, illustrating the importance of molecular physiological analyses of the function of individual ion channel genes (Hirsch et al., 1998; Gaymard et al., 1998).

Stomatal opening requires $K^+$ uptake into guard cells (Imamura, 1943; Humble et al., 1971; MacRobbie, 1983), which results in turgor and volume increases. $K^+_{in}$ channels have been suggested to function as a major pathway for $K^+$ uptake in guard cells during stomatal opening (Schroeder et al., 1994; Müller-Röber et al., 1998). A study with KAT1 knockout mutants may allow investigation of the in vivo role of KAT1 in guard cells. By screening all publicly available T-DNA pools, only one line was found with a T-DNA insertion in the 3' untranslated region of KAT1, which did not affect KAT1 expression.

In the present study, an approach was pursued using dominant negative $K^+_{in}$ channel mutants, which has, in addition to analysis of a null phenotype, allowed "titration" of $K^+_{in}$ channel activity in vivo to analyze effects of partial $K^+_{in}$ current reduction on stomatal and whole plant responses. In addition, this approach has an advantage over $K^+_{in}$ channel knockout mutants if $K^+_{in}$ channel α subunits are redundant, as the dominant negative $K^+_{in}$ channel mutants used here can form nonfunctional heteromultimeric channel proteins with $K^+_{in}$ channel α subunits in situ (Baizabal-Aguirre et al., 1999). Data showed that dominant negative KAT1 mutants effectively suppress the activity of AKT2 channels, even though AKT2 channels were shown to include instantaneous currents and a near linear steady-state current-voltage relationship at negative potentials (Baizabal-Aguirre et al., 1999), which differs dramatically from KAT1 properties (Schachtman et al., 1992). Note that statements that instantaneous AKT2 currents have been overlooked are incorrect (Marten et al., 1999).

Patch clamp studies on Arabidopsis guard cells showed that $K^+_{in}$ channel properties differ from KAT1 expressed in Xenopus oocytes, suggesting that additional subunits or regulators contribute to $K^+_{in}$ channels in vivo (Ichida et al., 1997). Together with KAT1, an Arabidopsis $K^+$ channel β subunit homolog (Tang et al., 1996) and other $K^+_{in}$ channel α subunits may constitute heteromultimeric $K^+_{in}$ channels in guard cells (Baizabal-Aguirre et al., 1999; Isacoff et al., 1990; Dreyer et al., 1997). The present study shows that regardless of subunit composition, the dominant negative point mutant kat1-T256R is able to suppress $K^+_{in}$ channel activity in guard cells in vivo.

To date, no single point mutations that suppress wild-type ion channel activity have been reported in plants. In mammals, only a few examples of dominant-negative $K^+$ channel suppression have been reported. In humans, the genetic disease, long QT syndrome, an inherited cardiac disorder which causes arrhythmia and sudden death, is associated with dominant missense mutations in cardiac $K^+$ channel genes (Curran et al., 1995; Sanguinetti et al., 1996; Doyle et al., 1998) that reduce $K^+$ current magnitudes up to by 79% (Sanguinetti et al., 1996). This suggests that long QT syndrome-associated mutations in $K^+$ channel genes have a dominant negative effect on $K^+$ channel function (Curran et al., 1995; Sanguinetti et al., 1996).

Figure 3:
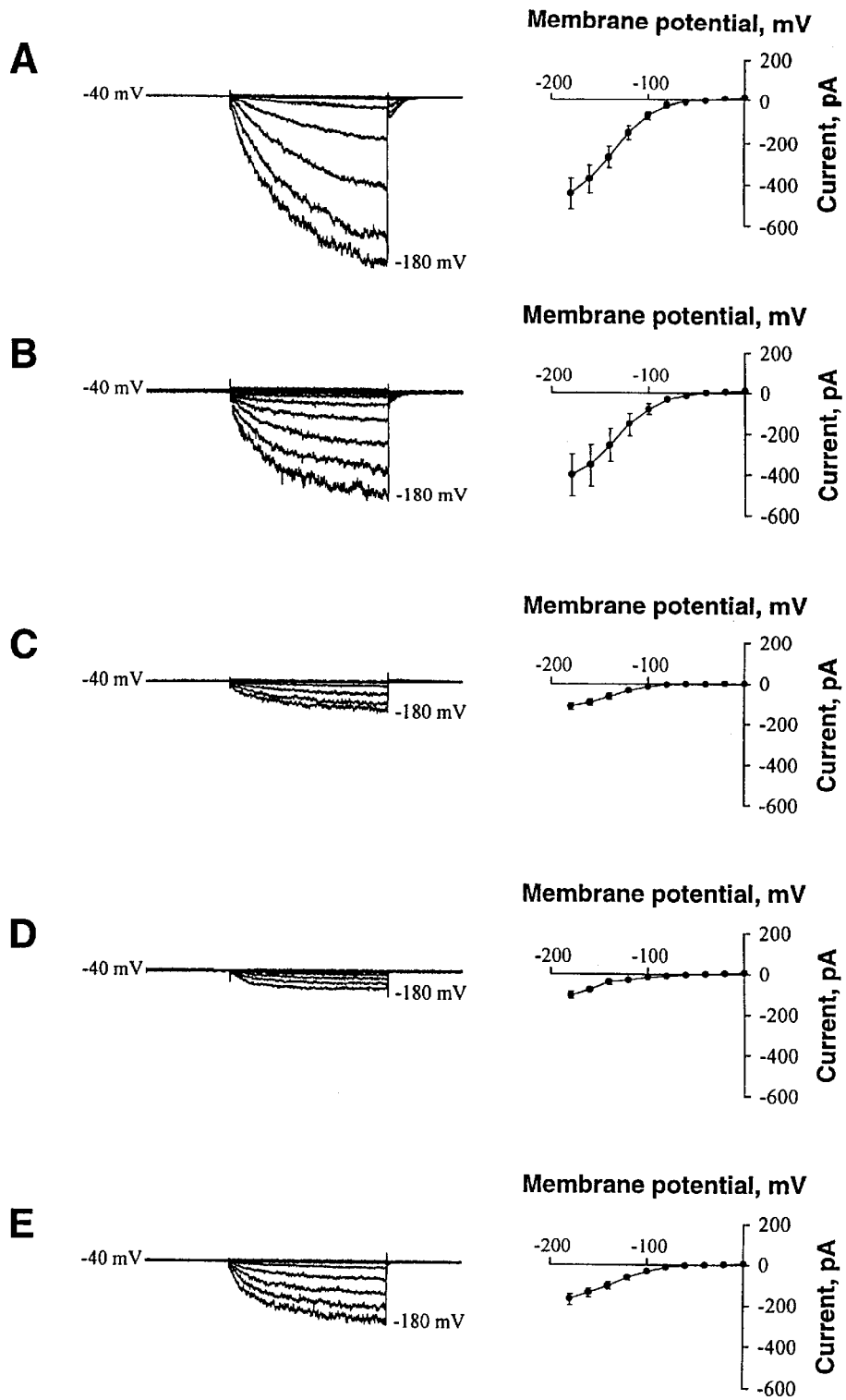
FIG. 3. Guard cells, from the two strong transgenic $K^+_{in}$ channel suppressor lines which show inhibition of light-induced stomatal opening, have significantly reduced $K^+_{in}$ currents compared to wild-type and vector-transformed control plants. (A) Inward $K^+$ currents (left) recorded in the presence of 30 mM KCl and current-voltage relationships (right, n=11) in wild-type guard cells. (B) Inward $K^+$ currents (left) recorded in the presence of 30 mM KCl and current-voltage relationships (right, n=5) in vector-transformed control guard cells. (C) Inward $K^+$ currents (left) recorded in the presence of 30 mM KCl and current-voltage relationships (right, n=14) in transgenic $K^+_{in}$ channel suppressor lines #15-4 guard cells. (D) Inward $K^+$ currents (left) recorded in the presence of 30 mM KCl and current-voltage relationships (right, n=10) in transgenic $K^+_{in}$ channel suppressor line #22-6 guard cells. (E) Inward $K^+$ currents (left) recorded in the presence of 30 mM KCl and current-voltage relationships (right, n=5) in transgenic line #23-4 guard cells. Membrane potentials were stepped from a holding potential of −40 mV to −180 mV in −20 mV increments. Data on right are mean ±SE.

$K^+_{in}$ Channel Activity Required for $K^+$ Uptake During Light-Induced Stomatal Opening When wild-type KAT1 and kat1-T256R cRNA were co-injected into Xenopus oocytes, reduction in $K^+_{in}$ currents by 75% was observed when the ratio of injected RNA concentration was about 1:1.5 for KAT1:kat1-T256R (Baizabal-Aguirre et al., 1999). $K^+_{in}$ currents were reduced by 75% in the #15-4 and #22-6 lines (FIG. 3). Therefore, the molar ratio of mRNA of wild-type KAT1 and KAT1 mutants can be estimated in the range of about 1:1.5 in guard cells of the two strong transgenic $K^+_{in}$ suppressor lines (#15-4 and #22-6).

Previous studies on $K^+_{in}$ channels have been performed with pharmacological blockers (Ichida et al., 1997; Kelly et al., 1995) which also affect other mechanisms in plant cells (Sheahan et al., 1993). To circumvent use of such blockers and to quantitatively titrate $K^+_{in}$ channel activity in guard cells, transgenic plants were generated that expressed dominant negative KAT1 mutants. Functional analyses of individual $K^+_{in}$ channel suppression lines were achieved through patch clamping of Arabidopsis guard cells, combined with stomatal physiology measurements, leaf water transpiration assays, plant growth analyses and analyses of $K^+$ uptake in guard cells. The phenotypes of individual lines were reproducible from generation to generation allowing quantitative analyses. Together the data provide unequivocal molecular evidence that $K^+_{in}$ channels mediate $K^+$ uptake during stomatal opening in response to light.

Interestingly, transgenic lines #3-17 and #23-4 in which $K^+_{in}$ currents were reduced by 39% and 58%, respectively (FIGS. 1B and 3E), did not show inhibition of light-induced stomatal opening (FIGS. 1C and 2A). In contrast, in the strong suppressor lines #15-4 and #22-6, even after 3 hours of light exposure stomatal apertures had not yet reached values of dark-treated controls (FIG. 2A). Comparison of vector-transformed, wild-type, and 4 different transgenic $K^+_{in}$ suppressor lines reveals that reduction in $K^+_{in}$ channel activity by up to 58% is not sufficient to affect light-induced stomatal opening, whereas reduction in $K^+_{in}$ channel activity by 75% causes clear impairment of light-induced stomatal opening under physiological conditions. Comparison of physiological stomatal responses in differentially suppressed lines as determined here, provides important data that can be used for quantitative integrated ("bioinformatic") models of stomatal movements.

Implication for $K^+_{in}$ Channel Regulation During Signal Transduction

Previous pharmacological blocker studies on *Vicia faba* and Arabidopsis guard cells resulted in estimates suggesting that reduction in $K^+_{in}$ channel activity by 50% would not affect stomatal opening and that $K^+_{in}$ channel activity needs to be down-regulated by about 85% to obtain a substantial effect on stomatal opening (Ichida et al., 1997; Kelly et al., 1995). The present study supports but also refines this hypothesis demonstrating that about 58% of $K^+_{in}$ channel inhibition does not greatly affect light-induced stomatal opening under the imposed conditions. However, reduction in $K^+_{in}$ channel activity by 75% impaired light-induced stomatal opening (FIGS. 2A and 3).

Figure 2:
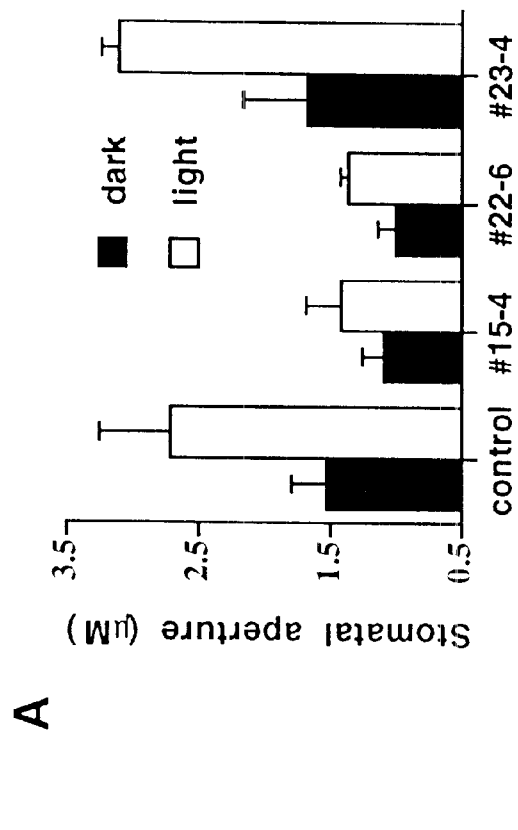
FIG. 2. Inhibition of light-induced stomatal opening and levels of transgenic dominant negative KAT1 transcripts in transgenic $K^+_{in}$ channel suppressor lines in which expression of dominant negative KAT1 mutants is driven by a tandem-repeat of the 35S promoter. (A) Stomatal aperture before treatment with stomatal opening conditions (solid bars; vector-transformed control, n=100; transgenic line #15-4, n=60; transgenic line #22-6, n=60; transgenic line #23-4, n=40). Stomata were incubated for 3 hours in 30 mM KCl (open bars; vector-transformed control, n=100; transgenic line #15-4, n=60; transgenic line #22-6, n=60; transgenic line #23-4, n=40). Error bars show SE. (B) RNA blot analysis of transgenic dominant negative KAT1 transcripts in wild-type controls (c) and in transgenic lines #15-4, #22-6 and #23-4. Total cellular RNA was extracted from leaves of plants, separated on a 1.2% denaturing agarose gel and then transferred onto a nylon membrane. The blot was probed with $^{32}$P-radiolabeled KAT1 cDNA. (C) The same blot as in (B) used for probing transgenic KAT1 transcripts was hybridized with $^{32}$P-radiolabeled 18S rDNA to show relative amounts of RNA samples loaded.
Figure 2:

Previous studies have shown that cytosolic second messengers such as $Ca^{2+}$, inositol-1, 4,5-triphosphate, and GTPγS inhibit $K^+_{in}$ channels in guard cells (Schroeder et al., 1989; Blatt et al., 1990; Fairley-Grenot et al., 1991; Luan et al., 1993; and Hoshi et al., 1995). Inhibition of $K^+_{in}$ channels by elevation of the cytosolic $Ca^{2+}$ concentration (Schroeder et al., 1989) correlates to external $Ca^{2+}$-induced inhibition of stomatal opening (DeSilva et al., 1985; MacRobbie, 1986). Down-regulation of $K^+_{in}$ channels in *Vicia faba* by the physiological stimulus ABA causes 57% to 75% reduction in $K^+_{in}$ channel activity (Blatt, 1990; Lemtiri-Chlieh et al., 1994; Schwartz et al., 1994), which alone would be close to the threshold for reducing $H^+$-drive $K^+$ uptake into guard cells and stomatal opening (FIGS. 1–3). The present data illustrate the importance of even partial $K^+_{in}$ channel down-regulation, because parallel modulation of $H^+$ pumps (Kinoshita et al., 1995) and other mechanisms (e.g., anion channel regulation) (Schwartz et al., 1995), can synergistically regulate $K^+$ uptake via $K^+_{in}$ channels.

Reduction in $K^+_{in}$ Channel Activity by 75% Reduces Water Loss and Increases Plant Growth at Reduced Water Supply The reduction of $K^+_{in}$ currents in transgenic guard cells resulted in less water loss in detached leaves of the suppressor lines compared to vector-transformed controls (FIG. 5). Interestingly, the two suppressor lines also showed a clear enhancement in growth of whole plants when water supply was limited (FIGS. 6B, D) compared to vector-transformed control plants. Under well-watered conditions, growth of suppressor lines was not enhanced (FIGS. 6A, C). These data correlate to data showing reductions in transpirational water loss, in $K^+$ uptake and in stomatal opening in the suppressor lines. These data suggest that the two transgenic $K^+_{in}$ suppressor lines lose less water when water supply is limiting because stomata of the suppressor lines do not open widely, thus reducing dehydration.

Titration of $K^+_{in}$ channel activity by using dominant negative KAT1 mutants as shown here might provide an approach to modulate the degree of stomatal opening of certain plants, thus, allowing required $CO_2$ influx while reducing transpirational water loss.

In conclusion, the data described herein provide unequivocal molecular evidence for the model that $K^+_{in}$ channels mediate $K^+$ uptake in guard cells under physiological conditions and show that partial reduction in $K^+_{in}$ channel activity maintains Arabidopsis growth under limited watering conditions.

REFERENCES

Baizabal-Aguirre et al., *J. Mem. Biol.*, 167, 119 (1999).
Barnett et al., *Plant Physiol.* 41, 1222 (1966).
Bechtold et al., *C. R. Acad. Sci., Paris*, 316, 1194 (1993).
Bevan et al., *Nucl. Acid Res.*, 11, 369 (1983).
Blatt et al., *Nature*, 346, 766 (1990).
Blatt, *Planta*, 180, 445 (1990).
Boyer, In: *Water deficits and plant growth*, T. T. Kozlowski (ed.)., Academic Press, New York., pp. 154–190 (1976).
Cao et al., *Plant Physiol.*, 109, 1093 (1995).
Callis et al., *Genes Develop.*, 1, 1183 (1987).
Chasan, *The Plant Cell*, 4, 1463 (1992).
Curran et al., *Cell*, 80, 795 (1995).
Dellaporta et al., in *Chromosome Structure and Function*, pp. 263–282 (1988).
DeSilva et al., *New Phytol.*, 101, 555 (1985).
Doyle et al., *Trends Genet.*, 14, 92 (1998).
Dreyer et al., *Biophys. J.* 72, 2143 (1997).
Fairley-Grenot et al., *Plant Cell*, 3, 1037 (1991).
Findlay et al., *J. Memb. Biol.*, 139, 103 (1994).
Gallie et al., *The Plant Cell*, 1, 301 (1989).
Gassmann et al., *Plant Physiol.*, 105, 1399 (1994).
Gaymard et al., *Cell*, 94, 647 (1998).
Gordon-Kamm et al., *The Plant Cell*, 2, 603 (1990).
Green et al., *Stain Technology*, 65, 647 (1990).
Hayashimoto et al., *Plant Physiol.*, 93, 857 (1990).
Hinchee et al., *Biotech.*, 6, 915 (1988).
Hirsch et al., *Science*, 280, 918 (1998).
Hong et al., *Plant Physiol.*, 113, 1203 (1997).
Horsch et al., *Science*, 227, 1229 (1985).
Hoshi, *J. Gen. Physiol.*, 105, 309 (1995).
Humble et al., *Plant Physiol.*, 48, 447 (1971).
Ichida et al., *Plant Cell*, 9, 1843 (1997).
Ikuta et al., *Biotech.*, 8, 241 (1990).
Imamura, *Jap. J. Bot.*, 12, 251 (1943).
Isacoff et al., *Nature*, 345, 530 (1990).
Katz et al., *J. Gen. Microbiol.*, 129, 2703 (1983).
Kelly et al., *Plant J.*, 8, 479 (1995).
Kim et al., *Science*, 260, 960 (1993).
Kinoshita et al., *Plant Cell*, 7, 1333 (1995).
Kwak et al., *Planta*, 202, 9 (1997).
Jefferson, *Plant Molecular Biology Reporter*, 5, 387 (1987).
Joshi, *Nucl. Acid Res.*, 15, 6643 (1987).
Lang et al., *Plant Mol. Biol.*, 5, 951 (1992).
Laursen et al., *Plant Mol. Biol.*, 24, 51 (1994).
Lemtiri-Chlieh et al., *J. Memb. Biol.*, 137, 99 (1994).
Li et al., *Plant Physiol*, 116, 785 (1998).
Li et al., *Plant Physiol.*, 106, 963 (1999).
Luan et al., *Proc. Natl. Acad. Sci. USA*, 90, 2202 (1993).
Maathuis et al., *Planta*, 197, 456 (1995).
MacRobbie, *J. Exp. Bot.*, 34, 1695 (1983).
MacRobbie, in *Molecular and Cellular Aspects of $Ca^{2+}$ in Plant Development*, ed. Marme, T. a., Plenum, New York, pp. 383–384 (1986).
MacRobbie, *Phil. Trans. Roy. Soc. London*, 1374, 1475 (1998).
Marten et al., *Proc. Natl. Acad. Sci. USA*, 96, 7581 (1999).
McCabe et al., *Bio/Tech.*, 61, 923 (1988).
McElroy et al., *Molec. Gen. Genet.*, 231, 150 (1991).
Morison, in *Stomatal Function*, eds. Zeiger, E., Farquhar, G. D. & Cowan, I. R., Stanford University, Stanford, pp. 229–251 (1987).
Müller-Röber et al., *EMBO J.*, 14, 2409 (1995).
Müller-Röber et al., *J. Exp. Bot.*, 49, 293 (1998).
Murakami et al., *Mol. Gen. Genet.*, 205, 42 (1986).
Nakamura et al., *Plant Physiol.*, 109, 371 (1995).
Niedz et al., *Plant Cell Reports*, 14, 403 (1995).
Ow et al., *Science*, 234, 856 (1986).
Park et al., *Plant Physiol.*, 103 359 (1993).
Pei et al., *Plant Cell*, 9, 409 (1997).
Potrykus et al., *Mol. Gen. Genet.*, 199, 183 (1985).
Prasher et al., *Biochem. Biophys. Res. Comm.*, 126, 1259 (1985).
Roberts et al., *Plant J.*, 8, 811 (1995).
Sambrook et al., *Molecular Cloning: A Laboratory Manual*, Cold Spring Harbor, N.Y. (1989).
Sanguinetti et al., *Proc. Natl. Acad. Sci USA*, 93, 2208 (1996).
Schachtman et al., *Science*, 258, 1654 (1992).
Schroeder et al., *Nature*, 312, 361 (1984).
Schroeder et al., *Proc. Natl. Acad. Sci. USA*, 84, 4108 (1987).
Schroeder et al., *Nature*, 338, 427 (1989).
Schroeder et al., *Annu. Rev. Biophys. Biomol. Struct.*, 23, 441 (1994).
Schwartz et al., *Proc. Natl. Acad. Sci. USA*, 91, 4019 (1994).
Schwartz et al., *Plant Physiol.*, 109, 651 (1995).
Serageldin, World Bank, Washington, D. C., pp. 1–33 (1995).
Sheahan et al., *Plant J.*, 3, 647 (1993).
Skriver et al., *Plant Cell*, 2, 503 (1990).
Spencer et al., *Plant Mol. Biol.*, 18, 201 (1992).
Stalker et al., *Science*, 242, 419 (1988).
Sutcliffe, *PNAS USA*, 75, 3737 (1978).
Tang et al., *Plant Cell*, 8, 1545 (1996).
Terryn et al., *Plant Cell*, 5, 1761 (1993).
Thillet et al., *J. Biol. Chem.*, 263, 12500 (1988).
Twell et al., *Plant Physiol.*, 91, 1270 (1989).
Vasil et al., *Plant Physiol.*, 91, 5175 (1989).
Wegner et al., *Plant Phyisol*, 105, 799 (1994).
Zukowsky et al., *PNAS USA*, 80, 1101 (1983).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for increasing drought tolerance in a plant, comprising: inhibiting or disabling inward-rectifying potassium ($K^+_{in}$) channel activity in stomatal guard cells of the plant by expressing in the stomatal guard cells of the plant a recombinant DNA segment which encodes a plant $K^+_{in}$ channel protein, wherein the plant $K^+_{in}$ channel protein is KAT1, wherein the recombinant DNA segment comprises a dominant negative mutation in a codon for amino acid residue 256 or 262 of KAT1, and wherein the mutation encodes arginine at residue 256 or lysine at residue 262.

2. A method for inhibiting or reducing light-induced stomatal opening in a plant, comprising: inhibiting or disabling $K^+_{in}$ channel activity in the stomatal guard cells of the plant by expressing in the stomatal guard cells of the plant a recombinant DNA segment which encodes a plant $K^+_{in}$ channel protein, wherein the plant $K^+_{in}$ channel protein is KAT1, wherein the recombinant DNA segment comprises a dominant negative mutation in a codon for amino acid residue 256 or 262 of KAT1, and wherein the mutation encodes arginine at residue 256 or lysine at residue 262.

3. The method of claim 1 or 2 wherein the plant is a dicot.

4. The method of claim 1 or 2 wherein the plant is a monocot.

5. The method of claim 1 or 2 wherein the plant is a transgenic plant.

6. The method of claim 1 or 2 wherein transpirational water loss in the plant is decreased.

7. The method of claim 1 or 2 wherein $K^+$ uptake in the guard cells is decreased.

8. The method of claim 1 or 2 wherein stomatal aperture diameter is decreased.

9. A plant having increased drought tolerance due to inhibited or disabled $K^+_{in}$ channel activity in the stomatal guard cells of the plant, wherein the plant comprises recombinant DNA segment that encodes a plant $K^+_{in}$ channel protein, which is expressed in the guard cells involved in stomatal opening in an amount which inhibits or disables $K^+_{in}$ channel activity in the stomatal guard cells, wherein the plant $K^+_{in}$ channel protein is KAT1, wherein the recombinant DNA segment comprises a dominant negative mutation in a codon for amino acid residue 256 or 262 of KAT1, and wherein the mutation encodes arginine at residue 256 or lysine at residue 262.

10. The plant of claim 9 wherein the DNA segment encodes a KAT1 channel protein that is inactive or that exhibits reduced activity compared to the wild-type KAT1 channel protein.

11. The plant of claim 9 which comprises an isolated chimeric DNA construct comprising a promoter functional in plant cells operably linked to the recombinant DNA segment.

12. The plant of claim 9 which is a dicot.

13. The plant of claim 9 which is a monocot.

14. The plant of claim 11 wherein the promoter is a constitutive promoter.

15. The plant of claim 14 wherein the promoter is a tandem repeat of the 35S CaMV promoter.

16. An expression cassette comprising a nucleic acid segment which comprises a plant KAT1 channel protein gene that comprises a dominant negative mutation operably linked to a promoter functional in a plant cell, wherein the dominant mutation is in a codon for amino acid residue 256 or 262 of KAT1, and wherein the mutation encodes arginine at residue 256 or lysine at residue 262.

17. A method of preparing a transformed plant in which light-induced stomatal opening is inhibited or reduced, comprising:

(a) introducing to plant cells an expression cassette comprising a DNA segment which encodes a plant $K^+_{in}$ channel protein, so as to yield a transformed plant, the genome of which is augmented with the expression cassette, wherein the plant $K^+_{in}$ channel protein is KAT1, wherein the DNA segment comprises a dominant negative mutation in a codon for amino acid residue 256 or 262 of KAT1, and wherein the mutation encodes arginine at residue 256 or lysine at residue 262; and (b) identifying a transformed plant in which light-induced stomatal opening is inhibited or reduced relative to a corresponding non-transformed plant.

18. The method of claim 17 wherein the DNA segment encodes an α subunit of a KAT1 channel protein.

* * * * *

UNITED STATES PATENT AND TRADEMARK OFFICE
CERTIFICATE OF CORRECTION

PATENT NO. : 6,635,803 B1
DATED : October 21, 2003
INVENTOR(S) : Julian I. Schroeder, June M. Kwak and Victor M. Baizabal-Aguirre It is certified that error appears in the above-identified patent and that said Letters Patent is hereby corrected as shown below:

<u>Title page,</u>
Item [75], Inventors, insert -- Victor M. Baizabal-Aguirre, Morelia, Michoacan (MX) --.

Signed and Sealed this

Thirteenth Day of April, 2004

JON W. DUDAS
*Acting Director of the United States Patent and Trademark Office*